US00PP12550P2

(12) United States Plant Patent
Kaskel

(10) Patent No.: US PP12,550 P2
(45) Date of Patent: Apr. 16, 2002

(54) HEMEROCALLIS PLANT NAMED 'CALYPSO QUEEN'

(75) Inventor: Mathew Kaskel, Homestead, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/657,546

(22) Filed: Sep. 8, 2000

(51) Int. Cl.[7] ..... A01H 5/00
(52) U.S. Cl. ..... Plt./312
(58) Field of Search ..... Plt./312

*Primary Examiner*—Bruce R. Campell
*Assistant Examiner*—June Hwu
(74) *Attorney, Agent, or Firm*—Foley & Lardner

(57) ABSTRACT

A new and distinct cultivar of Hemerocallis named 'Calypso Queen' characterized by its gold-orange colored flowers with a red eye-zone which are borne on branched scapes. The flowers do not fade in warm, bright conditions and are resistant to water spotting. Plants of 'Calypso Queen' bloom very early in the season, and then repeatedly throughout the growing season. Plants of 'Calypso Queen' are evergreen, thus they are attractive in landscapes. The plant grows vigorously, and propagates easily by division or tissue culture.

2 Drawing Sheets

BACKGROUND OF THE INVENTION

The present invention comprises a new and distinct cultivar of Hemerocallis plant, hereinafter referred to by the cultivar name 'Calypso Queen'. The genus Hemerocallis is a member of the family Liliaceae.

Hemerocallis comprises a genus of approximately 15 species of clump-forming, herbaceous perennials which are native to central Europe, China, and particularly, Japan. The flowers of Hemerocallis are lily-like and are borne in succession atop tall, frequently-branched scapes. Individual flowers last one day; thus, Hemerocallis is commonly known as 'Daylily' in commercial trade.

In recent years, Hemerocallis has been extensively hybridized, and many cultivars exist. Hemerocallis hybrids are hardy spring- and summer-blooming plants which are particularly well-adapted to landscape plantings.

The plants form clumps of fan-shaped crowns of vertically-ranked, keeled, strap-like leaves. Plants (individual crowns) range in size from approximately 20 cm to over 90 cm in spread. Depending upon the parentage, *Hemerocallis* hybrids may be deciduous, evergreen or semi-evergreen.

Hemerocallis hybrids come in a range of colors including orange, yellow, pink, reddish or purplish. The flowers are funnel-shaped or campanulate with six segments joined at the base into a tube.

Asexual propagation of Hemerocallis is frequently done by division. Propagation can also be done through the use of tissue culture practices.

The new cultivar 'Calypso Queen' is a product of a planned breeding program and was originated by the inventor, Matthew Kaskel, from a cross made during such a program in Homestead, Fla. in April of 1996. The male and female parents are proprietary Hemerocallis×hybrid unnamed seedling selections designated by number codes which are maintained by the inventor and used for breeding purposes only. The selection comprising the new variety was chosen after commencement of flowering of the progeny in April of 1997 and was originally identified by the number code #97-08. After more thorough commercial evaluation, the cultivar was given the name 'Calypso Queen'.

Asexual propagation of the new cultivar by tissue culture and divison was performed by the inventor in Homestead, Fla., and has demonstrated that the combination of characteristics as herein disclosed for the new cultivar 'Calypso Queen' are firmly fixed, reproduces true to type, and are retained through successive generations of asexual reproduction.

BRIEF DESCRIPTION OF THE INVENTION

The following traits have been repeatedly observed and are determined to be basic characteristics of 'Calypso Queen' which is combination distinguish this Hemerocallis as a new and distinct cultivar:

1. flowers are bright gold-orange with a red eye-zone;
2. flowers do not fade in warm, bright conditions and are resistant to water spotting;
3. individual scapes are relatively short and branched with many buds which open in succession for approximately 4 weeks. Subsequent scapes develop quickly after the initial scapes flower out;
4. spent flowers shrivel, become inconspicuous, drop from the scape quickly, and do not interfere with the opening of subsequent flowers;
5. plants begin blooming very early-season (March–April) and rebloom throughout a 90-day blooming season;
6. plants grow vigorously and propagate readily by division and tissue culture; and
7. plants have narrow evergreen foliage making them attractive in landscapes even when not in bloom.

The new cultivar is similar to its parent cultivar, however, 'Calypso Queen' has more intense flower coloration, is more floriferous, and begins blooming earlier in the season than either parent. Additionally, 'Calypso Queen' grows more vigorously and is more prolific when propagated, than its parents. The flowers of 'Calypso Queen' are similar to those of 'Southern Sparkle' (co-pending U.S. Plant patent application Ser. No. 09/657,543), however the colors of 'Calypso Queen' are considerably more intense, the base color is near orange and the eye zone darker rosy red. Plants of 'Calypso Queen' are considerably more likely to bloom and rebloom than 'Southern Sparkle'.

'Calypso Queen' has not been observed under all possible environmental conditions. The phenotype of the new cultivar may vary significantly with variations in environment such as temperature, light intensity, daylength and humidity, without any change in genotype.

BRIEF DESCRIPTION OF THE DRAWINGS

The accompanying color photographic illustrations show typical characteristics of Hemerocallis 'Calypso Queen', with colors being as nearly true as possible with illustrations of this type.

Sheet 1 shows a 10-month-old plant of 'Calypso Queen' grown from tissue culture and flowering in a landscape setting.

Sheet 2 is a close-up view showing the characteristics of the flowers and scape.

DETAILED BOTANICAL DESCRIPTION

The following observations, measurements and values describe 10 month old plants derived from a tissue culture plantlet, grown in Sebring, Fla., under landscape conditions which closely approximate those generally used in horticultural practice. Color references are made to The Royal Horticultural Society (R.H.S.) Colour Chart, except where general color terms of ordinary significance are used.

Classification:

*Commercial.*—Hemerocallis cv. 'Calypso Queen'.

*Genus/species.*—Hemerocallis×hybrid.

Parentage:

*Male parent.*—Unnamed proprietary selection of Hemerocallis.

*Female parent.*—Unnamed proprietary selection of Hemerocallis.

Propagation: Vegetative, by crown division.

Plant:

*Form/growth habit.*—Clump-forming; fan-shaped crowns of vertically ranked, opposite, smooth, keeled, ligulate leaves.

*Height.*—Approximately 46 cm to 50 cm including inflorescence.

*Width.*—Approximately 60 cm to 72 cm.

Foliage:

*Size.*—Mature leaves are approximately 42 cm to 50 cm and 1.7 cm to 2.2 cm wide (flattened).

*Shape.*—The leaf blade is ligulate with an acute tip. The margins are entire. The leaves are curved over their length. The leaf is keeled and arches downward.

*Surface texture.*—The leaf blade is thin with a smooth surface.

*Color.*—The leaves are medium-green throughout. The upper surfaces are greener than, but closest to, RHS 137 B, and lower surfaces are RHS 137 C. The margins of the leaf bases may be flushed and striated with RHS 184 D.

*Average number.*—The plant produces approximately 5 pairs of leaves before producing an inflorescence.

*Dormancy.*—Plants are evergreen and require no dormant period. If grown in appropriate conditions, plants are capable of growing year-round. If grown in locations with freezing winter conditions, the existing foliage will be cold-damaged, but the rhizome and roots will survive and resume producing new leaves with the arrival of warm spring weather.

Inflorescence:

*Borne.*—Flowers are borne in succession with new buds opening daily atop a 1- or 2-branched scape. Scapes may produce approximately 8–10 buds with each branch having 3–4 buds.

*Shape.*—Upright terminally branched determinant panicle bearing 8–10 flowers which open daily in succession.

*Buds.*—Dimensions: Approximately 6.0 cm long and 1.95 cm wide. Color: Yellow-orange, RHS 22 C–RHS 22 D, striated with RHS 146 C and with green, RHS 146 A, sepal tips.

*Individual flowers.*—Dimension: The diameter of the flower is approximately 9.7 cm to 10.2 cm (not flattened). The flower depth is 5.5 to 6.0 cm. The sepals and petals are reflexed outward. The sepals are approximately 7.65 cm long and 3.4 cm wide and are ovate in shape. The petals are approximately 7.0 cm long, 5.1 cm wide and are obovate in shape. Individual flower parts flattened for measurement. Shape: Funnel-form to campanulate; ovate or obovate and moderately reflexed. The three petals are slightly ruffled along the margins. The three sepals are slightly wavy along the margins. The petal and sepal apex shape is cuspidate. Color: Upper Surface: Sepals are yellow-orange, RHS 21 A–RHS 21 C, with RHS 169 B eye zone. Base of sepal is RHS 146 D. Petals are yellow-orange, RHS 21 A–RHS 21 C, with redder than, but closest to RHS 178 B eye zone. Base of petal (throat) is RHS 146 D. Lower Surface: Sepals are entirely yellow-orange, RHS 21 A–RHS 21 C. Base of sepal is RHS 146 D and tip of sepal is RHS 146 A. Petals are entirely yellow-orange, RHS 21 A–RHS 21 C. Base of petals is flushed with RHS 146 D. Texture: Moderately thick and leathery. Quantity: Approximately 8–10 flowers/buds present depending on the size of plant and inflorescence. Branch spikes contain approximately 3 to 4 flowers/buds.

*Senescent flower.*—Spent flowers collapse and shrivel, becoming inconspicuous and eventually falling from the scape in 1 or 2 days.

*Scape.*—The scape is approximately 46 cm to 50 cm in height, 6 mm in diameter when measured at midpoint, and darker than, but closest to, RHS 137 A in color.

*Bracts.*—Small leaf-like bracts are present at the junctions of the branches and the scape and also the flower buds and the scape. The bracts are variable in size, 5 cm to 10 cm long, and are RHS 137 A in color, both upper and lower surfaces.

*Time of blooming.*—In mature plants, flowering begins approximately early season (March 15 as observed in Sebring, Fla.).

*Duration of blooms.*—Individual flowers last 1 day, and the total duration of flowering is about 90 days with subsequent scapes appearing through out the growing season.

*Fragrance.*—Sweetly fragrant.

Reproductive organs:

*Ovary.*—Superior, oblong, 8 mm long and 4 mm wide, RHS 146 B–RHS 146 C.

*Pistil.*—1 per flower, 9.4 cm long, style 2.0 mm wide; RHS 22 C .

*Stamens.*—Six present, filament is flat, curved, and 4.8 cm long and 2 mm wide, RHS 23 A–RHS 23 C.

*Anthers.*—8 mm long, brown-black in color.

*Pollen.*—RHS 21 A.

Seed characteristics: Capable of producing viable see, 3 to 6 shiny black seeds per chamber, 4 mm to 5 mm, mostly round, often oblong, variably shaped.

Fruit characteristics: 3 valved, loculicidal capsule, 2.3 cm wide and 2.9 cm long, color RHS 146 B, becoming tinged with yellow, RHS 19 C when ripe.

Roots: Thick, fleshy, white roots with fine laterals.

Cultural:

*USDA zone.*—Grows and blooms best when grown in USDA Zones 6 to 11.

*Diseases/pests.*—No particular sensitivity to pests or diseases. Aphids may occasionally infest the plants during the winter months.

I claim:

1. A new and distinct cultivar of Hemerocallis plant named 'Calypso Queen' as illustrated and described.

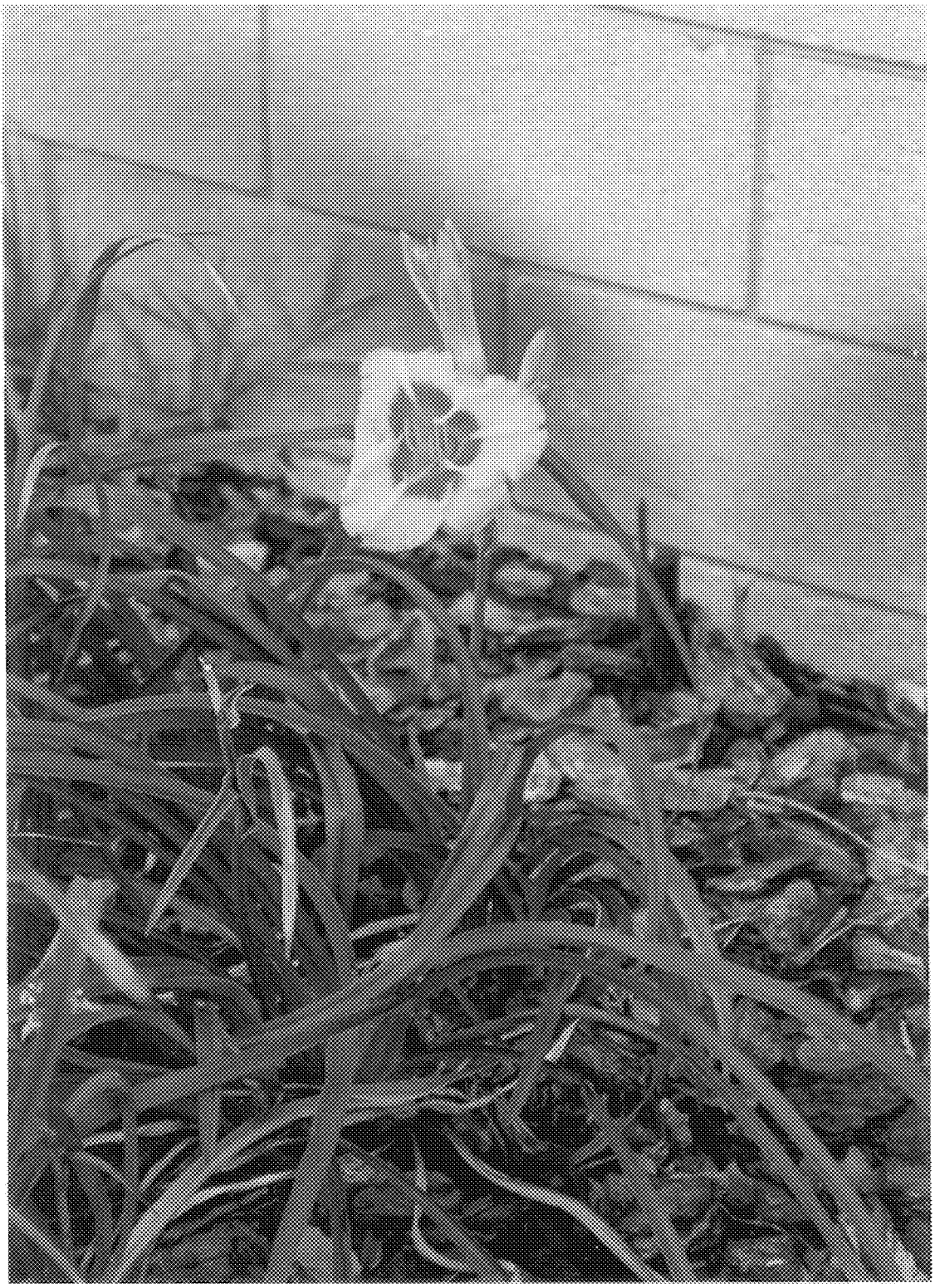

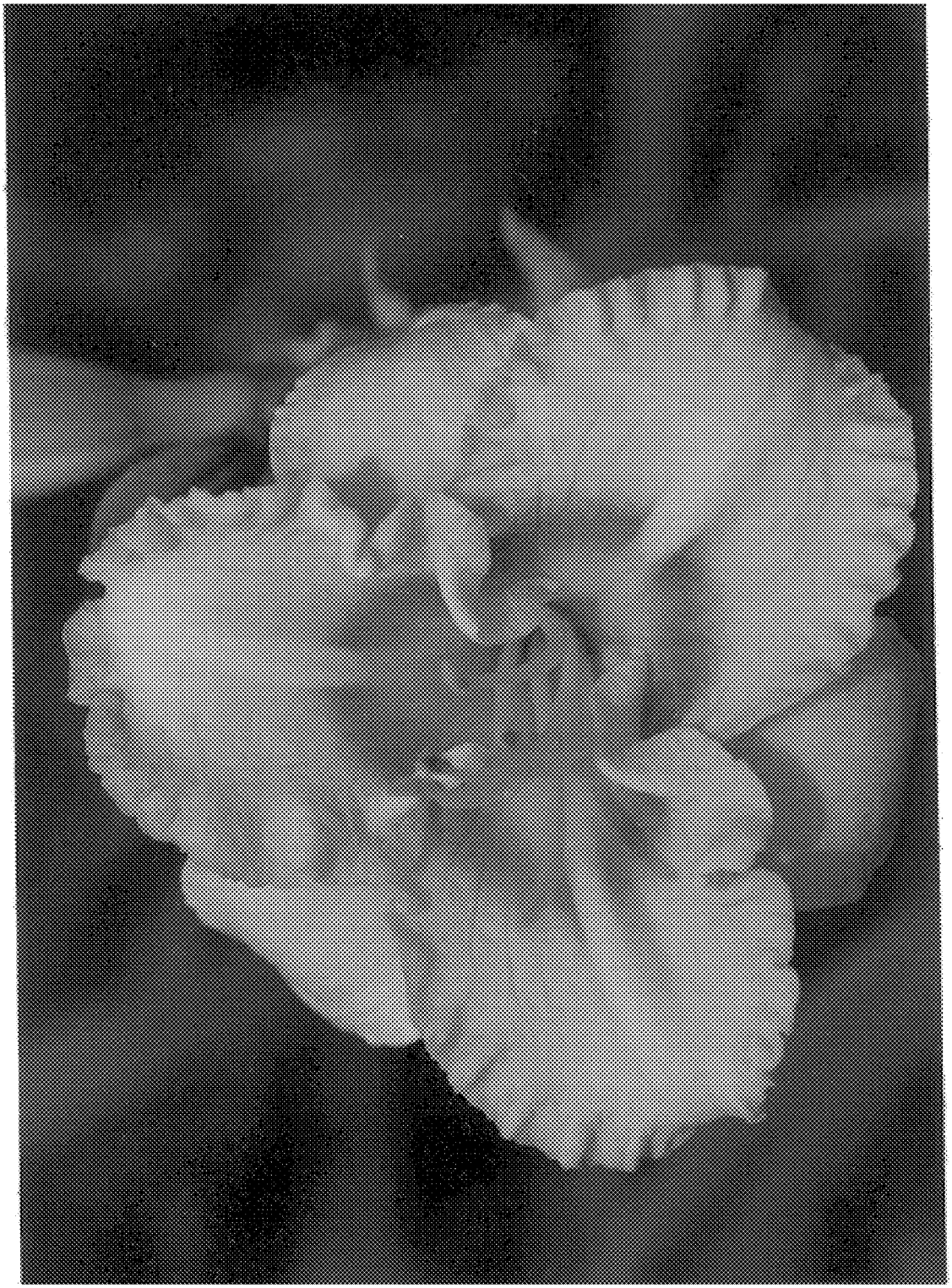

* * * * *